(12) United States Patent
Myklebust et al.

(10) Patent No.: US 6,306,107 B1
(45) Date of Patent: Oct. 23, 2001

(54) SYSTEM FOR MEASURING AND USING PARAMETERS DURING CHEST COMPRESSION IN A LIFE-SAVING SITUATION OR A PRACTICE SITUATION, AND ALSO APPLICATION THEREOF

(75) Inventors: Helge Myklebust; Helge Fossan, both of Stavanger (NO)

(73) Assignee: Laerdal Medical AS (NO)

( * ) Notice: Subject to any disclaimer, the term of this patent is extended or adjusted under 35 U.S.C. 154(b) by 0 days.

(21) Appl. No.: 09/576,820

(22) Filed: May 24, 2000

(30) Foreign Application Priority Data

May 31, 1999 (NO) .......................................... 2611

(51) Int. Cl.⁷ .................................................. A61B 5/103
(52) U.S. Cl. ............................ 600/587; 600/595; 128/897
(58) Field of Search ............................. 600/587, 595; 601/41; 607/5, 6; 128/897, 898

(56) References Cited

U.S. PATENT DOCUMENTS

| 4,095,590 | * | 6/1978 | Harrigan | 601/1 |
|---|---|---|---|---|
| 4,237,872 | * | 12/1980 | Harrigan | 601/1 |
| 4,797,104 | | 1/1989 | Laerdal et al. | 434/265 |
| 4,915,635 | * | 4/1990 | Ingenito et al. | 434/396 |
| 5,496,257 | | 3/1996 | Kelly | 60/41 |
| 5,589,639 | * | 12/1996 | D'Antonio et al. | 73/724 |
| 5,851,193 | | 12/1998 | Arikka et al. | 600/595 |
| 6,125,299 | * | 9/2000 | Groenke et al. | 607/6 |
| 6,141,584 | * | 10/2000 | Rockwell et al. | 607/5 |
| 6,148,233 | * | 11/2000 | Owen et al. | 607/5 |
| 6,174,295 | * | 1/2001 | Cantrell et al. | 601/41 |
| 6,178,357 | * | 1/2001 | Gliner et al. | 607/142 |

* cited by examiner

*Primary Examiner*—Robert L. Nasser
*Assistant Examiner*—Charles Marmor, II
(74) *Attorney, Agent, or Firm*—Nixon & Vanderhye PC (57) ABSTRACT

A system for measuring parameters during chest compression in a life-saving situation or a practice situation is provided, in which a pressure pad containing e.g. an accelerometer and a force activated switch (SW), as well as a calculation unit (B), is positioned on a patients chest, alternatively on or inside a manikin's chest, in order to register parameters such as depression distance, duration or rate of depressions during chest compression.

21 Claims, 6 Drawing Sheets

SYSTEM FOR MEASURING AND USING PARAMETERS DURING CHEST COMPRESSION IN A LIFE-SAVING SITUATION OR A PRACTICE SITUATION, AND ALSO APPLICATION THEREOF

BACKGROUND OF THE INVENTION

Field of the Invention

The present invention regards a system for measuring and using parameters during chest compression in a life-saving situation or a practice situation. The system may be connected to devices for performance feedback, in order to increase quality and efficiency.

Chest compression is a part of cardio-pulmonary resuscitation (CPR). CPR is described as life-saving first aid, and is part of the treatment given in case of sudden cardiac death. The compression depth is an important parameter during chest compression, which distance is given in centimeters in the CPR guidelines. Up until now, it has not been possible to measure this quantity in a sensible manner in connection with chest compressions on humans. In practice situations involving manikins on the other hand, it is common practice to measure and feed this information back to the lifesaver. Through practicing chest compression on a manikin, the lifesaver should be capable of repeating the same movement pattern on humans. Two facts make this difficult: First of all, studies show that a lot of people's ability to repeat this movement pattern is poor already immediately after being trained. Likewise, studies show that the ability to repeat the movement pattern is lessened further over time. Secondly, people who are to be given chest compressions will offer different degrees of resistance to the depression, as the human anatomy varies. As such, an assessment of the compression depth cannot be made on the basis of the force applied. The quality of the chest compression will be completely dependent on the ability of the rescuer to transfer what he or she has learned in the practice situation, and his or her ability to judge the depth and rate of compressions.

Studies in several countries have looked at the connection between the quality of cardiopulmonary resuscitation (CPR) and survival. These have indicated that the survival rate increases by a factor of 3–4 in the case of high quality CPR.

BRIEF SUMMARY OF THE INVENTION

The object of the present invention is therefore to make it possible to improve the quality of chest compressions, such that a larger number of patients survive.

The above is provided through a device of the type mentioned initially, the characteristics of which can be seen from claim 1. Further characteristics of the invention can be seen from the remaining, dependent claims.

Feedback may be in the form of a visual representation or in the form of corrective and instructive voice messages to the user; or the feedback may be forwarded to an emergency center that can interpret the situation and guide the user during the life-saving. The data collected, or the feedback, may also be stored in order to provide documentation of the treatment administered to the patient, and may if necessary be compared with the CPR guidelines, for the purpose of improving the training system if possible.

The device according to the invention may be integrated in a defibrillator (AED) or be part of a device that measures and feeds back information regarding both compression and ventilation, or be a stand-alone device that only performs compression measurements and provides feedback, or it may form that part of the manikin sensor system which measures and registers chest compression.

BRIEF DESCRIPTION OF THE DRAWINGS

In the following, the invention will be described in greater detail with reference to the drawings, in which.

DETAILED DESCRIPTION OF THE INVENTION

Figure 6:
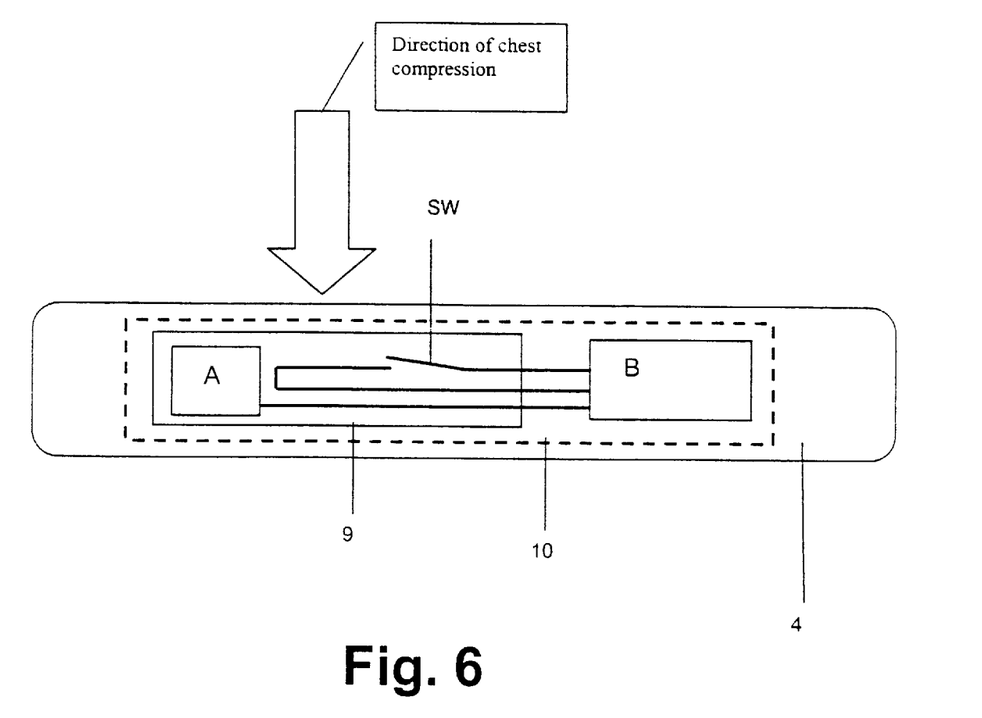
FIG. 6 shows the principles of construction for the pressure pad

The device may consist of a pad 4 that is connected to the patient's chest, the pad 4 having a supply cable with a terminal 1 for connection to electrodes 2. The top of the pad may be provided with instructions for placement of the pad in relation to the patient's nipples. The pad 4 provides a marker indicating where the lifesaver should put his hands in order to administer compressions, and also contains a sensor unit 9 for measuring depression, and possibly an additional sensor for the applied force. The sensor unit 9 consists of an accelerometer A and a force activated switch SW, and is connected to a calculation unit B in the form of for instance an electronic circuit. The force activated switch SW can be in the form of a membrane switch, and is arranged in the sensor unit 9 so that the applied vertical force is activating it. Together, the sensor unit 9 and the calculation unit B form the compression unit 10, see also FIG. 6.

Accelerometer A may be of the type ADXL202 marketed by "Analog Devices", and may be provided on a printed circuit board arranged at right angles to the surface of the pad on which the lifesaver puts his hands. Upon depression of the pad, the printed circuit board with the accelerometer will move, and the sensor will deliver an acceleration signal.

The depression is obtained by integrating the acceleration twice. In order to produce this result only, the initial parameters are set to zero at time t=0.

The two integrations yield:

$\eta(acceleration)dt = Velocity + V_0$ Velocity at time t=0: $V_0=0$. (1)

$\eta(acceleration)dt = Distance + D_0$ Displacement at time t=0: $D_0=0$ (1)

In practice, this means that an integration circuit must be given the message to start the integration just as the depression commences. This will minimize integration errors caused by other factors.

The force activated switch SW being activated when the compression starts, or when the applied force measured exceeds a predetermined force can effect this.

The first solution of the integral gives the velocity, or speed, plus the initial velocity $V_0$, the initial velocity $V_0$ being equal to zero when the integration commences upon activation of the switch, see also equation (1). The integration of the resulting velocity gives the displacement plus the initial position $D_0$. The initial position is equal to zero when the integration commences upon activation of the switch; see also equation (2).

Figure 2:
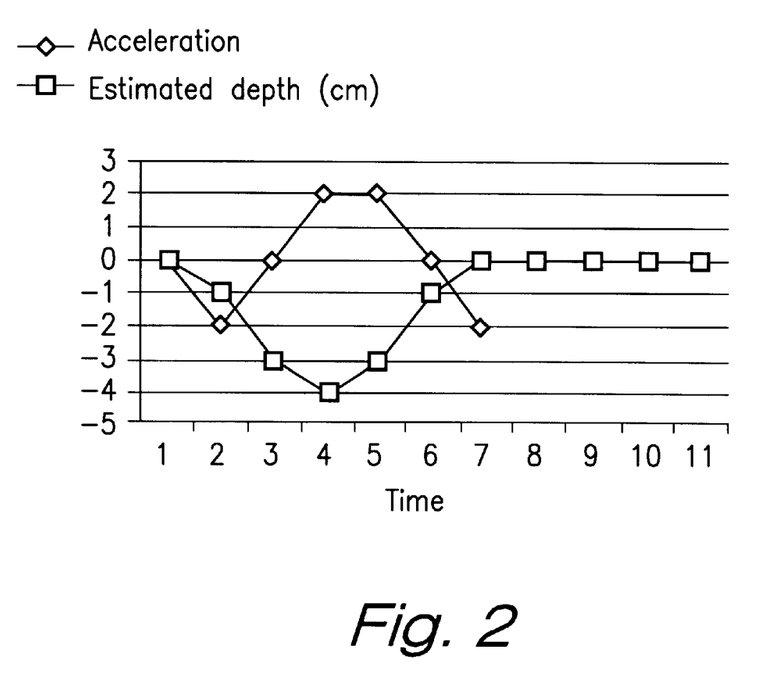
FIG. 2 shows a curve diagram of measurement values relative to chest displacement.

The estimated displacement (distance) $S_n$ is given by the following equation, which is deduced from the above integrals:

$$s_n \cong s_{n-1} + \left(\frac{1}{2} \cdot a_n \cdot t_s^2\right) + t_s^2 \cdot (a_o + a_1 + a_2 + \ldots a_{n-1}) \qquad (3)$$

in which n is the sample number, $a_n$ is the acceleration, and $t_s$ is the sample interval Table I shows calculations performed by use of the rule in equation (3), where $t_s$ is 1. FIG. 2 shows the curve for the values in Table I.

TABLE I

| Sample values | Acceleration [cm/s²] | Calculation of depression $S_n$ [cm] |
|---|---|---|
| $A_0$ | 0 | 0 |
| $a_1$ | −2 | −1 |
| $a_2$ | 0 | −3 |
| $a_3$ | 2 | −4 |
| $a_4$ | 2 | −3 |
| $a_5$ | 0 | −1 |
| $a_6$ | −2 | 0 |
| $a_7$ | 0 | 0 |
| $a_8$ | 0 | 0 |
| $a_9$ | 0 | 0 |
| $a_{10}$ | 0 | 0 |

If an accelerometer measuring the acceleration along two axes is used, the accelerometer may be oriented so as to let one measurement axis represent the vertical acceleration and the other the horizontal acceleration. Horizontal acceleration is undesirable, as it indicates that the applied chest compression is not vertical. In case of such an indication, the device will be able to give feedback to the user to the effect that the chest compression must be performed vertically.

This technique will be usable with other sensors, such as dynamometers, in order to obtain additional parameters for quality improvement.

Figure 1:
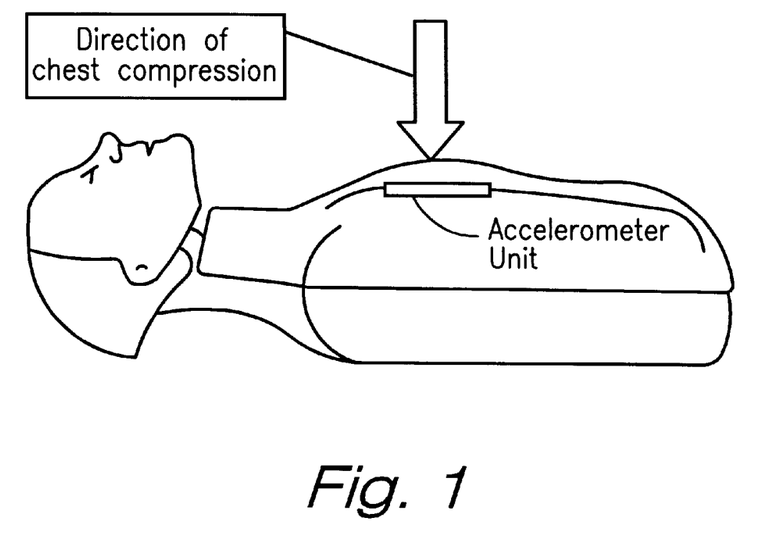
FIG. 1 schematically shows a manikin with a compression unit for implementation of the invention.

Above, the invention has been described as used on a patient. However it will also be possible to use the invention for training purposes, by arranging the compression unit 10 unit either on or in a manikin, see FIG. 1. The accelerometer can then be mounted on a plate in the manikin, which plate follows the chest compression in such a manner that the vertical acceleration indicates chest compression. Lung inflations can be measured by having the rising of the chest that is caused by the expansion of the manikin lungs act on an arm that rotates the plate on which the accelerometer is mounted, about an axis. Thereby the effect of gravity, g, on the accelerometer will cause the signal value to change. The compression unit 10 may also be used directly on the outside of the manikin, as if it were a patient. In this case, horizontal acceleration will indicate shaking in the manikin device. A force activated switch will also be provided here, in order to indicate the start of a chest compression, and the same calculations as mentioned above may be used to give an indication of the depression.

Using the unit according to the invention inside a manikin is advantageous when compared with previously used devices, as the new unit takes up little space compared with previously used units, which often consist of a toothed rack that co-operates with a sliding potentiometer in order to measure the displacement, and which becomes relatively large in size, thus leaving little space for other manikin equipment that is required in order to practice CPR and register all activity on the manikin.

Figure 3:
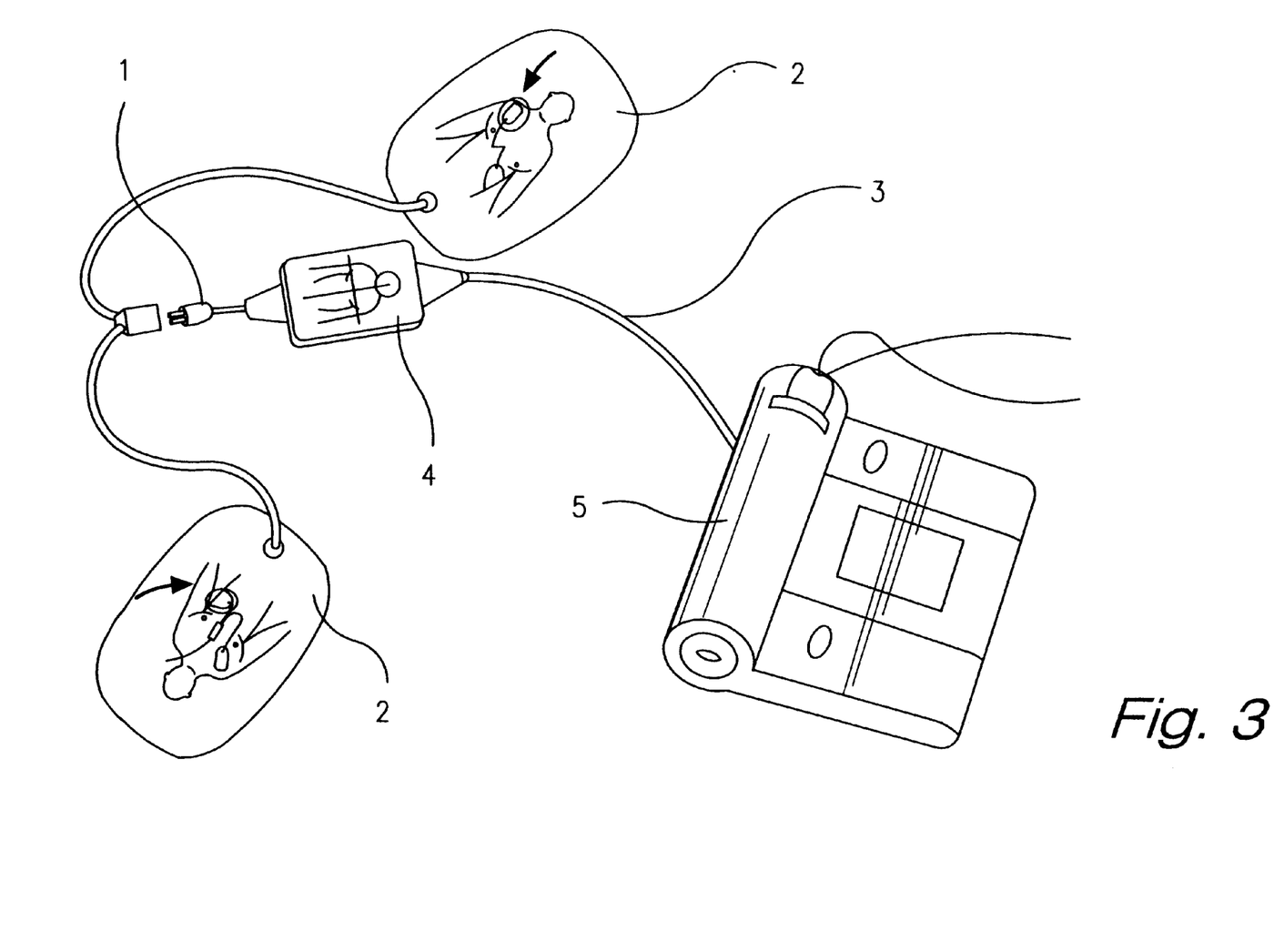
FIG. 3 schematically shows a pressure pad containing the compression unit connected to the defibrillator patient cable.
Figure 4:
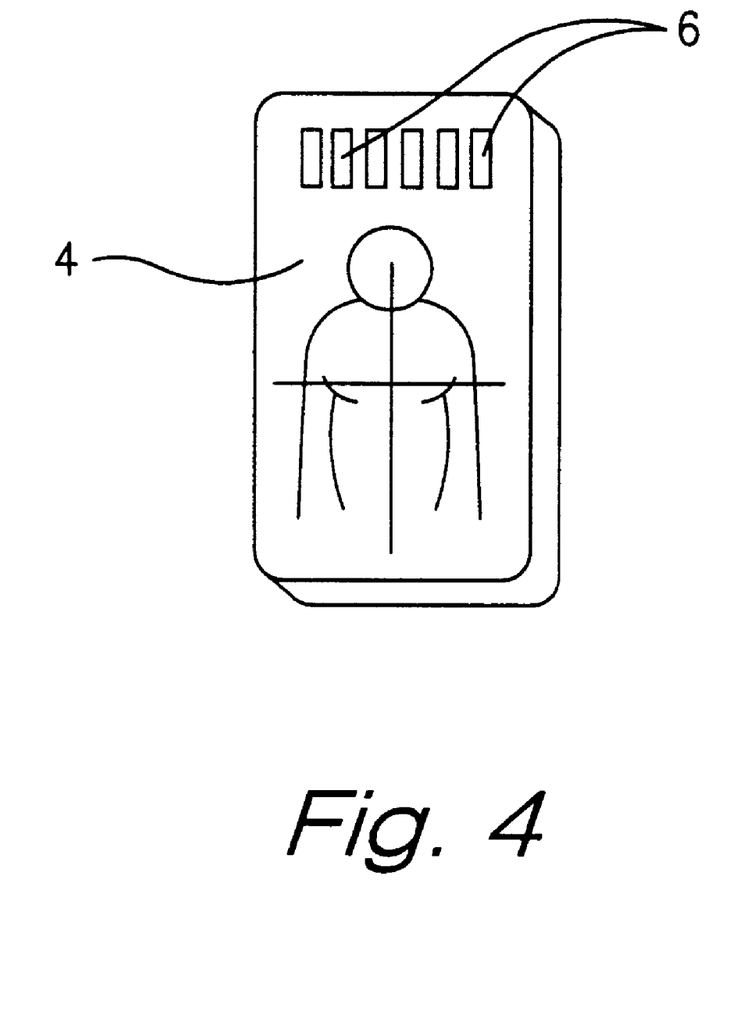
FIG. 4 schematically shows an embodiment in which the pressure pad containing the compression unit is a stand-alone unit.

The measured values can be transmitted to a separate calculation unit B that may be arranged in the pressure pad, as indicated in FIG. 4, or the measurement values are transmitted directly via separate supply leads 3 directly to a defibrillator 5 that employs its built-in CPU in order to perform the calculations, see also FIG. 3. Said calculation unit B may for instance consist of a CPU unit and associated components for performing the calculations, and is technically considered to be prior art that anyone who is skilled in the art may implement. As such, it does not form part of the invention, and is not described in greater detail herein. When using a standard defibrillator 5 that is appropriate for this purpose, the information unit in this may be used to guide the lifesaver.

When using a stand-alone unit, this must be equipped with a separate CPU in order to perform the calculations, as well as a separate information unit. This information unit may simply consist of light-emitting diodes (LEDs) 6 as indicated in FIG. 4. In the unit shown in FIG. 4, the electronics and indicators are built into a pressure pad 4, which is provided with markings that show where on the patient the pressure pad should be placed and where the chest compression should be carried out. The light-emitting diodes may for instance indicate depression by one diode lighting up for each centimeter. When the depression exceeds 5 cm, the color changes e.g. from green to red.

Figure 5:
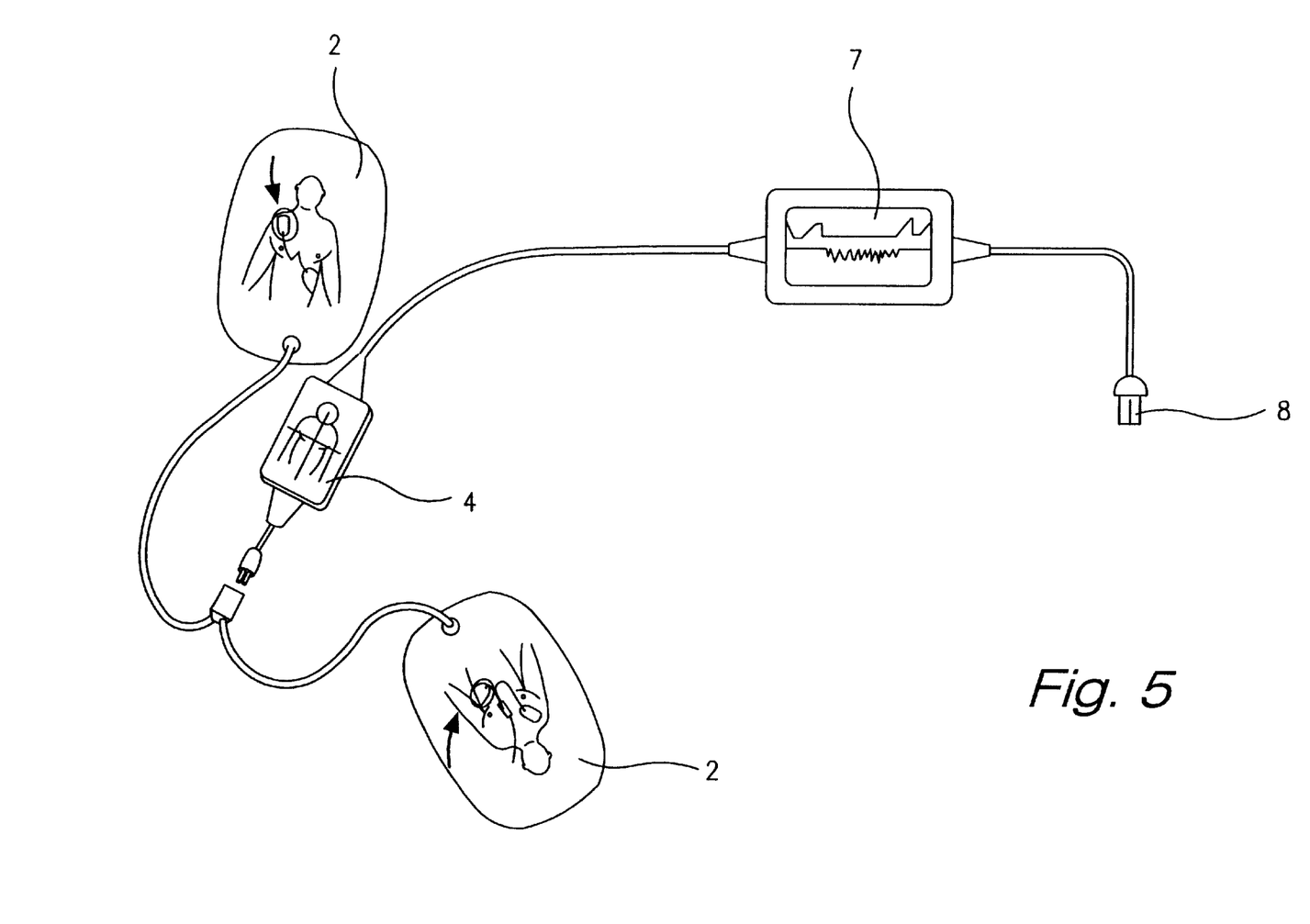
FIG. 5 shows a second embodiment of the pressure pad containing the compression unit.

FIG. 5 shows another possible embodiment of the invention, in which the pressure pad 4 has an outlet that can be connected to a display unit 7, for instance a screen, in order to provide feedback and possibly instructions. The estimated compression depth Sn being shown as indicated by the curve Sn in FIG. 2. It may also show the inflations to the patient during the CPR. The inflation signal is produced in a known manner per se, by the display unit containing a measurement system that measures the impedance between the electrodes 2, and in which inflation causes a change in this impedance. The display unit 7 may also consist of a screen and a loudspeaker that provides feedback in the form of speech or sound signals, or a loudspeaker unit on its own. Instead of a separate display unit or in addition to the separate display unit, a computer may be connected for further processing of the data, or a modem or similar may be connected for transmission of data for instance to an emergency center.

FIG. 5 shows a connector 8 for connecting to the above-mentioned units or a defibrillator, which in addition to receiving the signals from the compression unit 4, also can receive signals (ECG) from the electrodes 2 or deliver electrical shocks via the electrodes 2.

Figure 7:
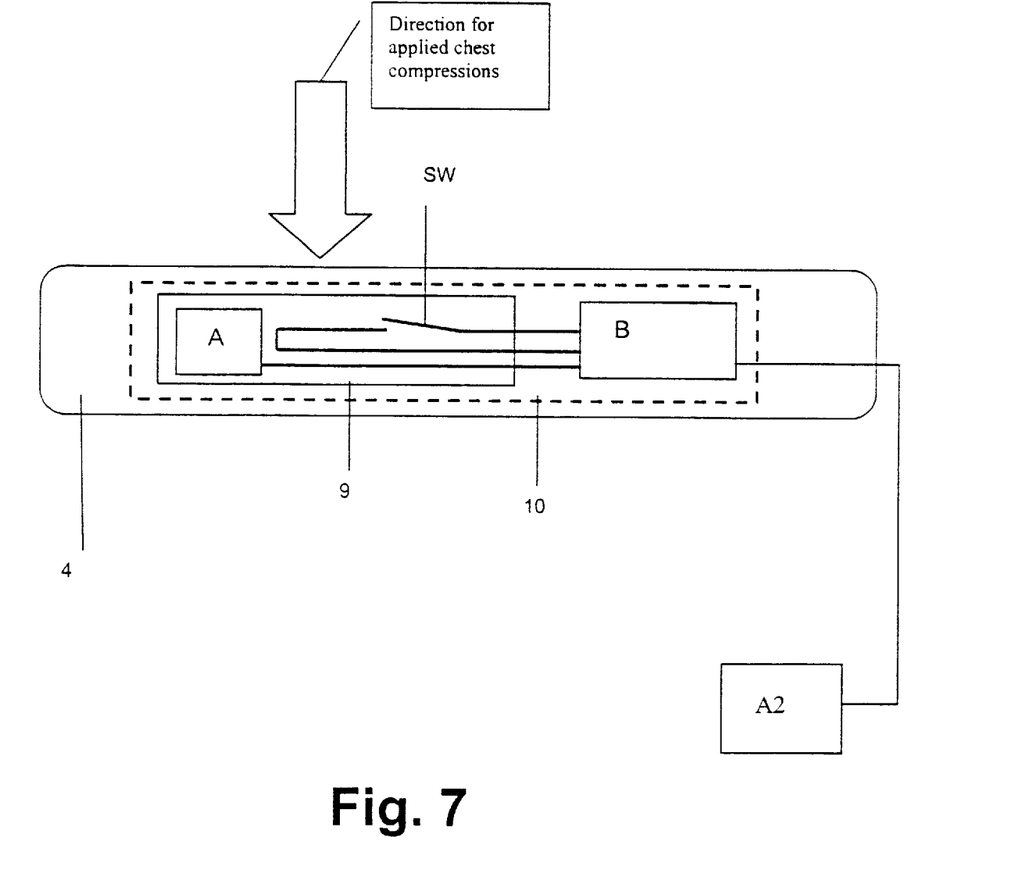
FIG. 7 shows the principal arrangement using two accelerometers in order to reduce measurement errors for chest compression performed during transport.

Occasionally, CPR must be performed during transportation, like in an ambulance, in a boat or aeroplane. In these conditions, the accelerometer A will also be affected by the overall vertical movement of the vehicle, thus introducing an integration error on estimated chest compression depth Sn. FIG. 7 shows the use of a second accelerometer A2, placed for instance within the defibrillator 5. This accelerometer is arranged to sense the vertical movement of the vehicle, and by subtracting the signal A2, from A2 from the signal A, from A using the calculation unit B, the integration error is significantly reduced.:

$$a_n = A_n - A2_n$$

What is claimed is:

1. System for measuring and using parameters when performing chest compression in a life-saving situation or a practice situation, comprising a calculation unit set to determine depression depth during compression by using signals from a sensor unit including a force activated switch set to respond when the depression commences, thereby indicating the start of the movement, and an accelerometer set to follow the movement of the chest.

2. System according to claim 1, wherein the sensor unit is placed inside a pressure pad adapted to be arranged on a patient's or manikin's chest.

3. System according to claim 2, wherein the pressure pad is provided with markings on top for guidance regarding placement on a patient's or manikin's chest.

4. System according to claim 2, wherein the calculation unit is an electronic circuit arranged in the pressure pad.

5. System according to claim 2, wherein the pressure pad contains a separate feedback unit, including at least one of light emitting diodes and an audio unit for providing at least one of feedback and instructions.

6. System according to claim 2, wherein the pressure pad includes an outlet for connection to a display unit for display of a curve showing the depression depth versus time.

7. System according to claim 6, wherein the display unit includes a loudspeaker unit for providing feedback and any instructions in the form of speech.

8. System according to claim 2, wherein an outlet in the pressure pad forms an interface to at least one of a defibrillator, a computer, and a modem.

9. System according to claim 1, wherein the calculation unit determines the approximate depression depth Sn according to the equation $$sn \approx sn - 1 + \left(\frac{1}{2} \cdot a_n \cdot t_s^2\right) + t_s^2 \cdot (a_o + a_1 + a_2 + \ldots a_{n-1})$$

in which n is the sample number, $a_n$ is the acceleration, and $t_s$ is the sample interval, the calculation being carried out for as long as the force activated switch is activated.

10. System for measuring and using parameters when performing chest compression in a life-saving situation or a practice situation, comprising a calculation unit set to estimate compression depth as a function of a difference in signals from a first accelerometer set to follow the movement of the chest, and a second accelerometer set to follow the movement of the patient.

11. System according to claim 10, wherein the first accelerometer is placed inside a pressure pad adapted to be arranged on a patient's or manikin's chest.

12. System according to claim 11, wherein the pressure pad is provided with marking on top for guidance regarding placement on a patient's or manikin's chest.

13. System according to claim 11, wherein the calculation unit is an electronic circuit arranged in the pressure pad.

14. System according to claim 11, wherein the pressure pad contains a separate feedback unit including at least one of light emitting diodes and an audio unit for providing at least one of feedback and instructions.

15. System according to claim 11, wherein the pressure pad includes an outlet for connection to a display unit for display of a curve showing the depression depth versus time.

16. System according to claim 15, wherein the display unit includes a loudspeaker unit for providing feedback and any instructions in the form of speech.

17. System according to claim 11, wherein an outlet in the pressure pad forms an interface to at least one of a defibrillator, a computer and a modem.

18. System according to claim 10, wherein the calculation unit determines the approximate depression depth Sn according to the equation $$sn \approx sn - 1 + \left(\frac{1}{2} \cdot a_n \cdot t_s^2\right) + t_s^2 \cdot (a_o + a_1 + a_2 + \ldots a_{n-1})$$

in which n is the sample number, $a_n$ is the acceleration, and $t_s$ is the sample interval, the calculation being carried out for as long as the force activated switch is activated.

19. A system comprising a sensor unit, including an accelerometer and a force activated switch connected to a calculation unit, that measures parameters including depression depth and depression rate when chest compression is performed in a life-saving situation or a practice situation, wherein the sensor unit and the calculation unit are arranged inside a pressure pad, together with means for providing at least one of visual and audio feedback regarding performance.

20. A system according to claim 19, wherein the sensor unit and the calculation unit are operatively connected to a defibrillator, and wherein the defibrillator provides feedback regarding the performance of the chest compression.

21. A system according to claim 19 wherein the sensor unit and the calculation unit are placed inside a manikin together with said means for providing at least one visual and audio feedback regarding performance.

* * * * *

UNITED STATES PATENT AND TRADEMARK OFFICE
CERTIFICATE OF CORRECTION

PATENT NO.    : 6,306,107 B1                                                  Page 1 of 1
DATED         : October 23, 2001
INVENTOR(S)   : Myklebust et al.

It is certified that error appears in the above-identified patent and that said Letters Patent is hereby corrected as shown below:

<u>Title page,</u>
Item [56], after last cited "U.S. PATENT DOCUMENTS", add:
--              FOREIGN PATENT DOCUMENTS
      WO     WO 00/27464           05/2000

OTHER PUBLICATIONS
Gruben et al; SYSTEM FOR MECHANICAL MEASUREMENTS DURING
CARDIOPULMONARY RESUSCITATION IN HUMANS"; IEEE Transactions on
Biomedical Engineering, Vol. 37, No. 2, February 1990; pp 204-209 --

Signed and Sealed this

Twelfth Day of August, 2003

JAMES E. ROGAN
*Director of the United States Patent and Trademark Office*